(12) United States Patent
Wang et al.

(10) Patent No.: US 6,567,204 B1
(45) Date of Patent: May 20, 2003

(54) ELECTROCHROMIC SOLUTION CONTAINING HYDRAZONE COMPOUND AND DEVICE MANUFACTURED WITH SAME

(75) Inventors: Fu-Shing Wang, Kaohsiung (TW); Kuang-Mei Hsu, Taipei (TW)

(73) Assignee: Exon Science, Inc. (TW)

( * ) Notice: Subject to any disclaimer, the term of this patent is extended or adjusted under 35 U.S.C. 154(b) by 0 days.

(21) Appl. No.: 09/946,063

(22) Filed: Sep. 4, 2001

(51) Int. Cl.$^7$ .......................... G02F 1/15; C07C 251/00
(52) U.S. Cl. .................. 359/265; 564/250; 564/251
(58) Field of Search .................. 564/251, 250; 548/427; 359/265, 266, 267, 268, 269, 270, 271, 272, 273, 274, 275

(56) References Cited

U.S. PATENT DOCUMENTS

| | | | |
|---|---|---|---|
| 4,365,014 A | 12/1982 | Sakai et al. | 430/59 |
| 4,902,108 A | 2/1990 | Byker | 350/357 |
| 5,239,405 A | 8/1993 | Varaprasad et al. | 359/272 |
| 5,446,577 A | * 8/1995 | Bennett et al. | 359/273 |
| 5,500,760 A | 3/1996 | Varaprasad et al. | 359/272 |
| 5,611,966 A | 3/1997 | Varaprasad et al. | 252/583 |
| 5,679,283 A | 10/1997 | Tonar et al. | 252/583 |
| 6,211,994 B1 | 4/2001 | Byker | 359/272 |
| 6,327,069 B1 | * 12/2001 | Allemand et al. | 359/265 |

FOREIGN PATENT DOCUMENTS

JP         62297382 A   * 12/1987   .......... C09K/9/02

OTHER PUBLICATIONS

Entwistle, Ian, et al., "Rapid Reduction of N–Nitrosoamines to N,N–Disubstituted Hydrazines; The Utility of Some Low–Valent Titanium Reagents," Tetrahedron, vol. 38, No. 3, pp. 419–423, 1982.

* cited by examiner

Primary Examiner—Hung Xuan Dang
Assistant Examiner—Tuyen Tra
(74) Attorney, Agent, or Firm—Madson & Metcalf

(57) ABSTRACT

An electrochromic solution includes a hydrazone compound as an anodic compound is disclosed. The hydrazone compound has a general formula (I)

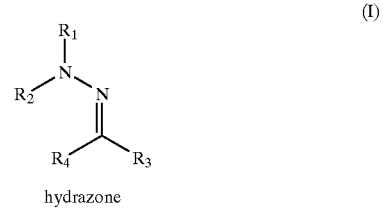

hydrazone wherein $R_1$, $R_2$, $R_3$ and $R_4$ are individually selected from a group consisting of hydrogen, alkyl containing 5 to 20 carbon atoms, alkenyl containing 2 to 20 carbon atoms, alkynyl containing 2 to 20 carbon atoms, and aryl containing 5 to 20 carbon atoms which are unsubstituted or optionally substituted with one or more ester, ether, aryl, amine, thioester, alkyl, alkoxy, alkene, alkyne, CN, F, Cl, Br, I and/or organometallcene functional group.

1 Claim, 1 Drawing Sheet

ELECTROCHROMIC SOLUTION CONTAINING HYDRAZONE COMPOUND AND DEVICE MANUFACTURED WITH SAME

FIELD OF THE INVENTION

The present invention relates to an electrochromic solution, and more particular to an electrochromic solution containing a hydrazone compound. The present invention also relates to an electrohromic device manufactured with the hydrazone-containing solution, which is adapted to be used in an electrochromic rearview mirror assembly.

BACKGROUND OF THE INVENTION

Glare is one of the troublesome factors when driving a vehicle. Many efforts have been made to solve the glaring problem. One of the most effective ways is to provide an electrochromic unit for the rearview mirror of the vehicle. The electrochromic unit deepens the color and thus reduces the reflection rate of the mirror accord to the degree of the glare, thereby minimizing the glaring effect. FIG. 1 is a schematic diagram showing a conventional electrochromic unit for use in a rearview mirror assembly of a vehicle to achieve the color-change purpose.

The electrochromic unit includes two glass substrates 11 and 12 positioned parallel to each other, and spaced apart by a distance of a micrometer-to-millimeter order. On each of the inner faces of the glass substrates, a transparent indium-tin-oxide (ITO) coating 13, 14 is provided as an electrode for electric conduction. The space 15 between the two glass substrates 11 and 12 is filled with an electrochromic solution and sealed with a material 16 inert to the electrochromic solution, e.g. epoxy. By applying a voltage across the ITO cathode and anode 13 and 14, the color of the electrochromic solution will change chemically. With the increase of the environmental light intensity, the voltage applied to the electrochromic unit increases, and the color of the mirror becomes darker.

In general, the electrochromic solution includes an anodic compound which undergoes a reversible color change when its valence state is altered due to oxidation, a cathodic compound which undergoes a reversible color change when its valence state is altered due to reduction, and a solvent which solubilizes the anodic and cathodic compounds but keeps chemically inert to the other constituents of the electrochromic solution. The electrochromic solution may optionally further includes an electrolyte material for enhancing the conductivity of the electrical current passing through the electrochromic solution. Please refer to U.S. Pat. Nos. 4,902,108, 5,679,283, 5,611,966, 5,239,405, 5,500,760 and 6,211,994B1 which are incorporated herein for reference, to realize examples of the anodic compound, cathodic compound, solvent and electrolyte material contained in conventional electrochromic solutions. In the prior art, the color change range of the electrochromic unit is from colorless to dark blue or dark blue-green, and the option of colors is quite limited. Further, when the voltage supply is removed, the color of the electrochromic unit is supposed to become colorless again. In practice, however, the color will not return colorless after a great number of color change cycles, but become pale yellow in stead. The rearview mirror thus looks somewhat dirty.

SUMMARY OF THE INVENTION

An object of the present invention is to provide an electrochromic solution which contains a photo-conductive compound as an anodic compound to enhance the color fixation thereof.

Another object of the present invention is to provide an electrochromic device which provides an alternative color option for a mirror.

A first aspect of the present invention relates to an electrochromic solution for use in an electrochromic unit for performing color change in response to a voltage applied to the electrochromic unit. The electrochromic solution includes at least one anodic compound, at least one cathodic compound and at least one solvent. The at least one anodic compound includs a hydrazone compound represented by the formula below:

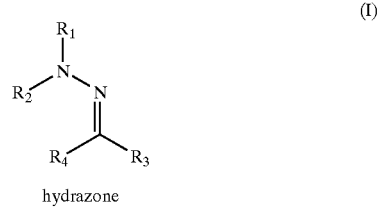

hydrazone wherein $R_1$, $R_2$, $R_3$ and $R_4$ are individually selected from a group consisting of hydrogen, alkyl containing 5 to 20 carbon atoms, alkenyl containing 2 to 20 carbon atoms, alkynyl containing 2 to 20 carbon atoms, and aryl containing 5 to 20 carbon atoms which are unsubstituted or optionally substituted with one or more ester, ether, aryl, amine, thioester, alkyl, alkoxy, alkene, alkyne, CN, F, Cl, Br, I and/or organometallcene functional group.

A second aspect of the present invention relates to an electrochromic device for use in a mirror for performing color change of the mirror in response to a voltage applied thereto. The electrochromic device includes a first transparent substrate; a second transparent substrate positioned substantially parallel to the first transparent substrate, and spaced apart from the first transparent substrate by a predetermined clearance to form a space therebetween; an electrochromic composition including a hydrazone compound, disposed in the space between the first and second transparent substrates; a seal disposed between the first and second transparent substrates for retaining the electrochromic composition in the space; and a pair of transparent electrodes provided on opposite surfaces of the first and second transparent substrates facing the space for providing the voltage for the electrochromic composition to perform color change.

A third aspect of the present invention relates to a hydrazone compound for use as a component of an electrochromic composition, represented by the formula (II):

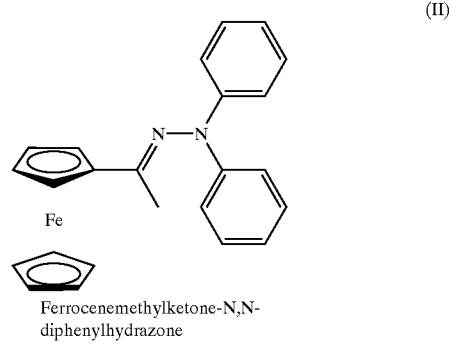

Ferrocenemethylketone-N,N-diphenylhydrazone wherein
respective aryl rings are individually unsubstituted or optionally substituted with one or more ester, ether, aryl, amine, thioester, alkyl, alkoxy, alkene, alkyne, CN, F, Cl, Br, I and/or organometallcene functional group.

BRIEF DESCRIPTION OF THE DRAWINGS

The present invention may best be understood through the following description with reference to the accompanying drawings, in which.

DETAILED DESCRIPTION OF THE PREFERRED EMBODIMENT

Figure 1:
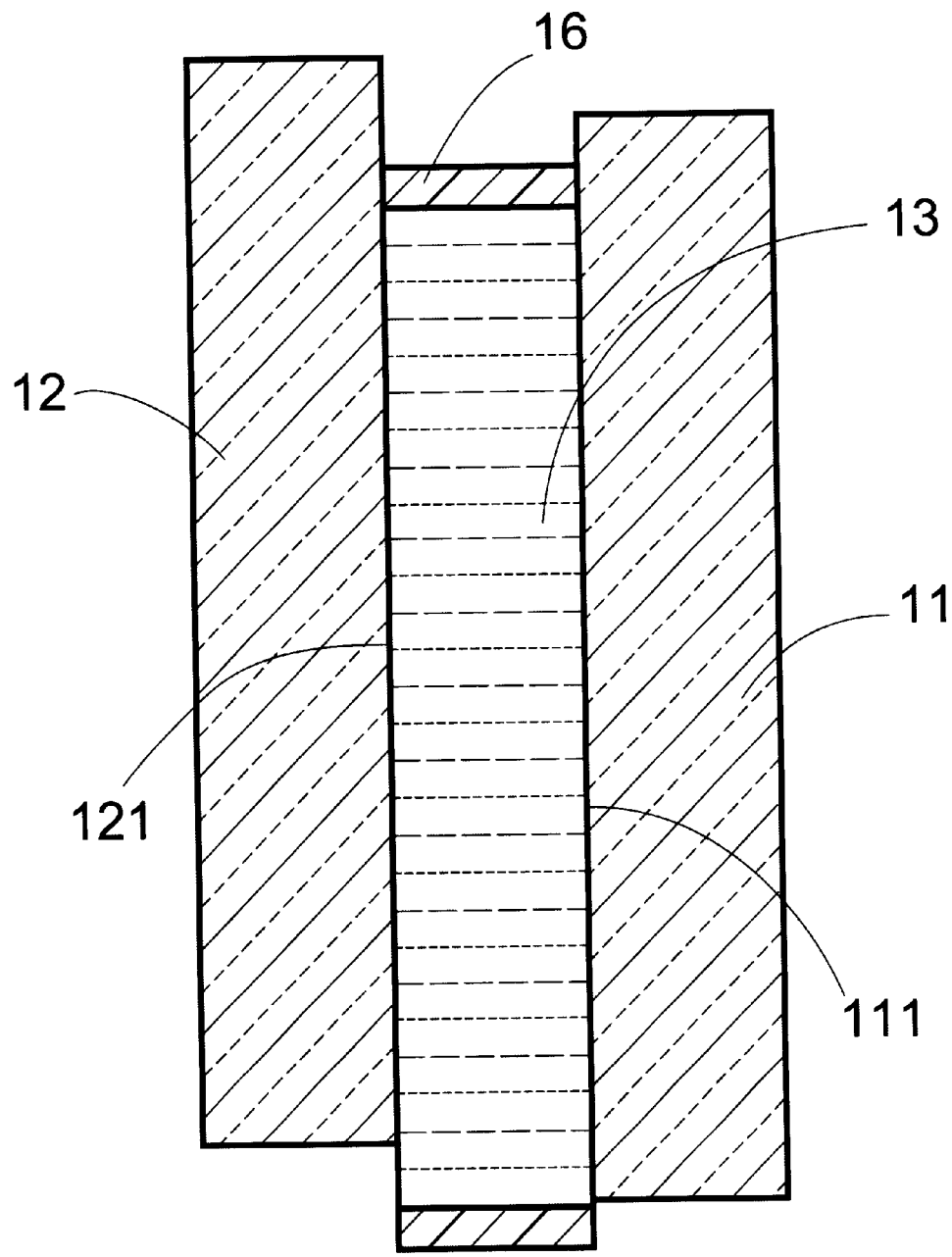
FIG. 1 is a schematic block diagram showing a conventional electrochromic unit for use in a rearview mirror assembly of a vehicle to achieve the color-change purpose.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The hydrazone compounds contained in the electrochromic solution of the present invention have been used in an electrophotographic photoconductor to form a photoconductive layer, referring to U.S. Pat. No. 4,365,014, which is incorporated herein for reference. As understood, the hydrazone compounds has good color fixation capability. The use of the hydrazone compounds in the electrochromic solution is thus advantageous for coloration properties. A few examples of the hydrazone compounds suitable for use as an anodic compound of the electrochromic solution are given below:

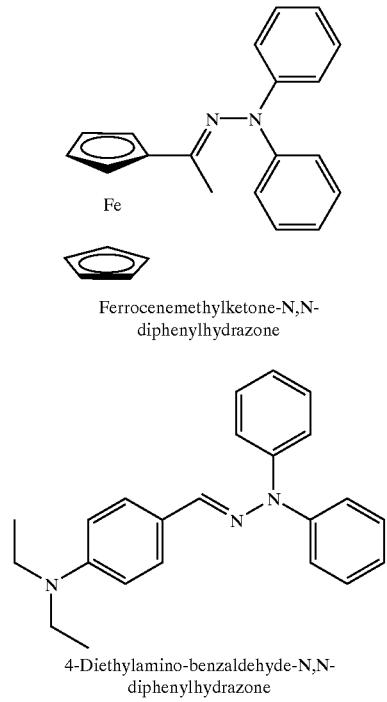

Ferrocenemethylketone-N,N-diphenylhydrazone (II)

4-Diethylamino-benzaldehyde-N,N-diphenylhydrazone (III)

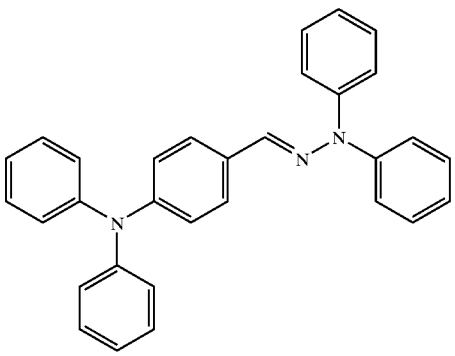

4-Diphenylamino-benzaldehyde-N,N-diphenylhydrazone (IV)

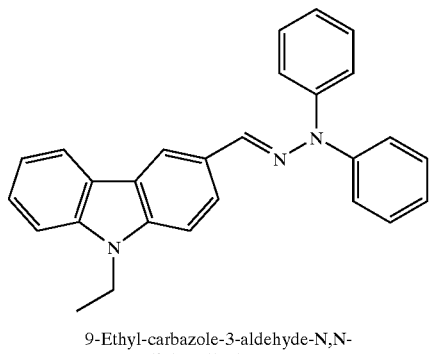

9-Ethyl-carbazole-3-aldehyde-N,N-diphenylhydrazone (V)

9-Ethyl-carbazole-3-aldehyde-N,N-methylphenylhydrazone (VI)

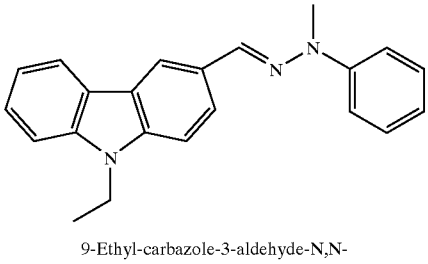

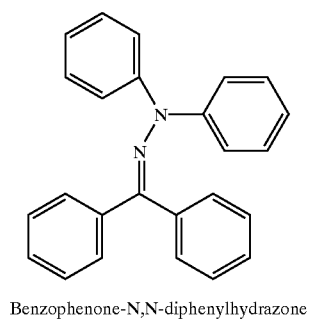

Benzophenone-N,N-diphenylhydrazone (VII)

In addition, acetone 2,2-dimethylhydrazone, 2-pentanone 2-ethyl-2-methylhydrazone, 2-ethylbutanal 1-ethyl-1-propylhydrazone, 2-ethyl-2-nonanone 2-hexyl-2-propylhydrazone, (E)-3-nonen-2-one 2-butyl-2-propylhydrazone, 2-hexanone 2-[(E)-2-butenyl]-2-[(Z)-2-butenyl]hydrazone, 4-pentyn-2-one 2,2-dipropylhydrazone, 1-penten-3-one 3,3-dimethylhydrazone, 2-hexanone 2,2-diphenylhydrazone, 3-heptanone 3-methyl-3-phenylhydrazone, 1-ethoxy-2-butanone 2-methyl-2-phenylhydrazone, 1-phenylacetone 2-(3-methoxyphenyl)-

2-phenylhydrazone, 2-phenacetaldehyde 1-methyl-1-phenylhydrazone, methyl 3-[(Z)-2-methyl-2-phenylhydrazone]-butanethioate, 1-(3-chlorophenyl)-3-methoxy-1-propanone 1-methyl-1-(3-methylphenyl) hydrazone, Ferrocenephenylketone 2-[(E)-2-butenyl]-2-[(Z)-2-butenyl]hydrazone, Bis(cyclopentadienyl) Cobaltmethylketone 2,2-diphenylhydrazone, Bis (cyclopentadienyl)dimethylzirconiummethylketone 2,2-diphenylhydrazone, 1-phenyl-1-ethanone 1,1-di(2-methoxyethyl)hydrazone, 1-[3-(dimethylamino)phenyl]-1-ethanone 1,1-diethylhydrazone, 2-[(Z)-2,2-diethylhydrazono]propyl cyanide, 2-[(E)-2-ethyl-2-phenylhydrazono]-3-methoxypropyl cyanide, (Z)-1-chloro-1-penten-3-one 3-methyl-3-phenylhydrazone and/or 2-propynal 1-[4-(dimethylamino)phenyl]-1-methylhydrazone can also be used for that purpose.

The hydrazone compounds (III), (IV), (V) and (VI) are commercially available from Syntax Corp. (Germany), and thus the synthesis processes thereof are not described here.

The hydrazone compound (II) is a novel compound which was prepared by reacting ferrocenemethylketone with N,N-diphenylhydrazine hydrochloride in ethanol reflux for 3 hours. Please refer to Entwistle and Johnstone, *Tetrahedron*, Vol. 38 (1982), pp. 419–423. The product was isolated to obtain Ferrocenemethylketone-N,N-diphenylhydrazone with a yield of 93%.

$^1$H-NMR (CDCl$_3$, 400 MHz), δ 7.29 (t, 4H), δ 7.11 (d, 4H), δ 7.04 (t, 2H), δ 4.78 (t, 2H), δ 4.39 (t, 2H), δ 4.17 (s, 5H), δ 2.0 (s, 3H).

The electrochromic solution of the present invention further includes a cathodic compound which can be any suitable compound conventionally used in the art. For example, a compound represented by the following formula can be used,

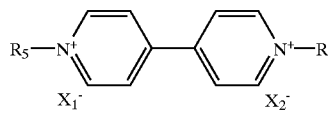

(VIII)

wherein

R5 and R6 are individually selected from a group consisting of alkyl containing 1 to 10 carbon atoms and aryl containing 5 to 20 carbon atoms which is unsubstituted or optionally substituted with alkyl, alkoxy, cyano, Cl, Br, I and nitro; and $X_1^-$ and $X_2^-$ are individually selected from a group consisting of Cl$^-$, Br$^-$, I$^-$, BF$_4^-$, PF$_6^-$, AsF$_6^-$, ClO$_4^-$ and NO$_3^-$.

Especially, the electrochromic solution includes a cathodic compound represented by the following formula:

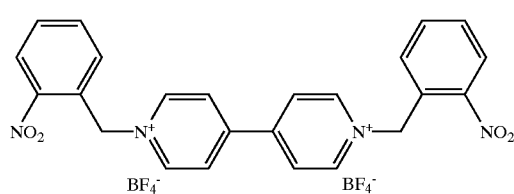

(IX)

Further, the electrochromic solution includes an electrolyte which can be any suitable compound conventionally used in the art. For example, Nafion, poly(2-acrylamide-2-methyl propane sulfonic acid) (PAMAS), poly(vinylalcohol phosphoric acid) (PAVA), poly(ethylene) oxide (PEO), poly (ethylene)imine (PEI), tetra-n-butylammonium fluorborate and/or polymethylmethacrylate (PMMA) can be used.

The anodic compound(s), cathodic compound(s) and electrolyte(s) are dissolved in a solvent selected from a group consisting of acetonitrile, N,N-dimethylformamide, propylene carbonate, methyl ethyl carbonate, 3-hydroxypropionitrile, ethylene carbonate and a mixture thereof.

The electrochromic solution includes the above components is filled into the space of the electrochromic unit similar to that shown in FIG. 1 to produce an electrochromic device. Examples are given as follows for illustration purposes only.

EXAMPLE 1

An electrochromic device was manufactured by disposing two sheets of glasses (10 cm×10 cm) spaced apart from each other to form a chamber therebetween, coating indium tin oxide (ITO) on the inner surfaces of both of the glasses, and filling the chamber with argon purged electrochromic solution consisting of 0.001~0.5 M 1,1'-bis(2-nitrophenyl)-4,4'-dipyridinium bis(tetrafluoroborate) (compound IX), 0.001~0.5 M Ferrocenemethylketone-N,N-diphenylhydrazone (compound II), and 0.05~5 wt % polymethylmethacrylate (PMMA) in a mixture of propylene carbonate (0~100% v/v) and ethyl methyl carbonate (100%~0% v/v).

By applying a voltage of 1~1.5 volts across the ITO electrodes of the electrochromic device, the solution, which initially appeared colorless, changed its color to a deep blue-purple color in 2~4 seconds. The device was open-circuited or short-circuited that the solution returned to its colorless state in 3~5 seconds. The device was cycled 50000 times at 30° C. between its transmittance at zero-applied potential and its stead-state transmittance with 1.0 volts applied thereto. The rate of changes in transmittance was unchanged after 50000 cycles.

On the other hand, after the device was cycled 24 hours at −30° C. with 1.0 volt, the solution change its color from colorless to deep blue-purple in 5 seconds, and returned colorless in 6 seconds. After the device was cycled 24 hours at 90° C. with 1.0 volt, the solution change its color from colorless to deep blue-purple in 3 seconds, and returned colorless in 3 seconds.

EXAMPLE 2

An electrochromic device was manufactured as described in Example 1 except that the electrochromic solution consists of 0.001~0.5 M 1,1'-bis(2-methoxyphenyl)-4,4'-dipyridinium bis(tetrafluoroborate), 0.001~0.5 M 4-diphenylamino-benzaldehyde-N,N-diphenylhydrazone (compound IV), and 0.05~5 wt % polymethylmethacrylate (PMMA) in a mixture of propylene carbonate (0~100% v/v) and ethyl methyl carbonate (100%~0% v/v).

By applying a voltage of 1~1.5 volts across the ITO electrodes of the electrochromic device, the solution, which initially appeared colorless, changed its color to a deep purple color in 2~6 seconds. The device was open-circuited or short-circuited that the solution returned to a light blue color in 3~6 seconds. The device was cycled 40000 times at 30° C. between its light blue state and its deep purple state with 1.1 volts applied thereto. The rate of changes in transmittance was unchanged after 40000 cycles.

EXAMPLE 3

An electrochromic device was manufactured as described in Example 1 except that the electrochromic solution consists of 0.001~0.5 M 1,1'-bis(2-methylphenyl)-4,4'-dipyridinium bis(tetrafluoroborate), 0.001~0.5 M 4-diphenylamino-benzaldehyde-N,N-diphenylhydrazone (compound IV), 0.001~0.5 M 5,10-dihydro-5,10-dimethylphenazine, and 0.05~5 wt % polymethylmethacrylate (PMMA) in a mixture of propylene carbonate (0~100% v/v) and ethyl methyl carbonate (100%~0% v/v).

By applying a voltage of 1~1.5 volts across the ITO electrodes of the electrochromic device, the solution, which initially appeared colorless, changed its color to a yellow green color, then blue color, and then deep purple color in 3~7 seconds. The device was open-circuited or short-circuited that the solution returned to a light blue color in 3~6 seconds. After the device was cycled 24 hours at −30° C. with 1.2 volts, the solution change its color to deep purple in 6 seconds, and returned to a light blue color in 5 seconds. After the device was cycled 24 hours at 90° C. with 1.0 volt, the solution change to a deep purple color in 4 seconds, and returned light blue in 3 seconds.

EXAMPLE 4

An electrochromic device was manufactured as described in Example 1 except that the electrochromic solution consists of 0.001~0.5 M 1,1'-bis(2-methylphenyl)-4,4'-dipyridinium bis(tetrafluoroborate), 0.001~0.5 M 9-ethyl-carbazole-3-aldehyde-N,N-diphenylhydrazone (compound V), and 0.05~5 wt % polymethylmethacrylate (PMMA) in a mixture of propylene carbonate (0~100% v/v) and ethyl methyl carbonate (100%~0% v/v).

By applying a voltage of 1~1.5 volts across the ITO electrodes of the electrochromic device, the solution, which initially appeared colorless, changed its color to deep purple in 3~5 seconds. The device was open-circuited or short-circuited that the solution returned to a light blue color in 3~6 seconds.

EXAMPLE 5

An electrochromic device was manufactured as described in Example 1 except that the electrochromic solution consists of 0.001~0.5 M 1,1'-bis(2-methylphenyl)-4,4'-dipyridinium bis(tetrafluoroborate), 0.001~0.5 M 4-diphenylamino-benzaldehyde-N,N-diphenylhydrazone (compound IV), and 0.0~5 wt % poly(ethylene)oxide (PEO) in a mixture of propylene carbonate (0~100% v/v) and ethyl methyl carbonate (100%~0% v/v).

By applying a voltage of 1~1.5 volts across the ITO electrodes of the electrochromic device, the solution, which initially appeared colorless, changed its color to deep purple in 4~7 seconds. The device was open-circuited or short-circuited that the solution returned to a light blue color in 4~5 seconds.

EXAMPLE 6

An electrochromic device was manufactured as described in Example 1 except that the electrochromic solution consists of 0.001~0.5 M 1,1'-bis(2-nitrophenyl)-4,4'-dipyridinium bis(tetrafluoroborate) (compound IX), 0.001~0.5 M 9-ethyl-carbazole-3-aldehyde-N,N-methylphenyhydrazone (compound VI), and 0.05~5 wt % polymethylmethacrylate (PMMA in a mixture of propylene carbonate (0~100% v/v) and ethyl methyl carbonate (100%~0% v/v).

By applying a voltage of 1~1.5 volts across the ITO electrodes of the electrochromic device, the solution, which initially appeared colorless, changed its color to brown-purple in 2~4 seconds. The device was open-circuited or short-circuited that the solution returned to colorless in 3~5 seconds.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A hydrazone compound for use as a component of an electrochromic composition, represented by the formula (II):

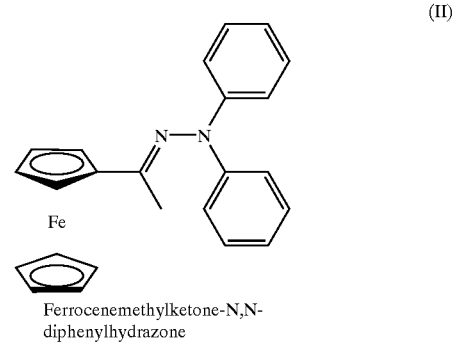

Ferrocenemethylketone-N,N-diphenylhydrazone wherein
respective aryl rings are individually unsubstituted or optionally substituted with one or more ester, ether, aryl, amine, thioester, alkyl, alkoxy, alkene, alkyne, CN, F, Cl, Br, I and/or organometallcene functional group.

* * * * *